US012178815B2

(12) United States Patent
Crauwels et al.

(10) Patent No.: US 12,178,815 B2
(45) Date of Patent: Dec. 31, 2024

(54) REGIMENS FOR TREATING HIV INFECTIONS AND AIDS

(71) Applicants: ViiV Healthcare Company, Wilmington, DE (US); Janssen Sciences Ireland Unlimited Company, County Cork (IE)

(72) Inventors: Herta Crauwels, Wilrijk (BE); David Margolis, Durham, NC (US); William R. Spreen, Durham, NC (US); Andrew Spaltenstein, Durham, NC (US); Peter Williams, Abington (GB)

(73) Assignees: ViiV Healthcare Company, Wilmington, DE (US); Janssen Sciences Ireland Unlimited Company (IE)

( * ) Notice: Subject to any disclaimer, the term of this patent is extended or adjusted under 35 U.S.C. 154(b) by 0 days.

(21) Appl. No.: 18/762,939

(22) Filed: Jul. 3, 2024

(65) Prior Publication Data

US 2024/0350486 A1    Oct. 24, 2024

Related U.S. Application Data

(63) Continuation of application No. 18/145,065, filed on Dec. 22, 2022, now abandoned, which is a continuation of application No. 16/631,868, filed as application No. PCT/IB2018/055349 on Jul. 18, 2018, now Pat. No. 11,564,921.

(60) Provisional application No. 62/535,302, filed on Jul. 21, 2017.

(51) Int. Cl.
| | |
|---|---|
| *A61K 31/4985* | (2006.01) |
| *A61K 9/00* | (2006.01) |
| *A61K 31/505* | (2006.01) |
| *A61K 31/7068* | (2006.01) |
| *A61K 31/7076* | (2006.01) |
| *A61P 31/18* | (2006.01) |

(52) U.S. Cl.
CPC ........ *A61K 31/4985* (2013.01); *A61K 9/0019* (2013.01); *A61K 31/505* (2013.01); *A61K 31/7068* (2013.01); *A61K 31/7076* (2013.01); *A61P 31/18* (2018.01)

(58) Field of Classification Search
CPC .............. A61K 31/4985; A61K 9/0019; A61K 31/505; A61K 31/7068; A61K 31/7076; A61P 31/18
USPC ........................................................ 514/46
See application file for complete search history.

(56) References Cited

U.S. PATENT DOCUMENTS

| | | | |
|---|---|---|---|
| 11,564,921 B2 * | 1/2023 | Crauwels ........... | A61K 31/4985 |
| 2002/0198388 A1 | 12/2002 | Hale et al. | |
| 2003/0207871 A1 | 11/2003 | Tung et al. | |
| 2004/0122000 A1 | 6/2004 | Hale et al. | |
| 2015/0313917 A1 | 11/2015 | Cai et al. | |
| 2017/0246118 A1 | 8/2017 | Johns | |

FOREIGN PATENT DOCUMENTS

| | | |
|---|---|---|
| EP | 06115938.0 | 12/2007 |
| WO | 2011/094150 A1 | 8/2011 |
| WO | 2016036759 A1 | 3/2016 |
| WO | 2016046786 A1 | 3/2016 |

OTHER PUBLICATIONS

ViiV Healthcare, ClinicalTrials.gov ID: NCT02120352, Version 24: Mar. 7, 2016. (Year: 2016).*
Crane et al. A Comparison of Adherence Timeframes Using Missed Dose Items and Their Associations with Viral Load in Routine Clinical Care: Is Longer Better? AIDS Behav (2017) 21:470-480. Published online: Oct. 6, 2016. (Year: 2016).*
U.S. Appl. No. 18/145,065, filed Dec. 22, 2022.
U.S. Appl. No. 16/631,868, filed Jan. 17, 2020.
Murray Miranda et al: "Satisfaction, Tolerability, and Acceptability of Cabotegravir (CAB)+ Rilpivirine (RPV) Long-Acting Therapy: LATTE-2 Results Acknowledgment", 21st International AIDS Conference, Jul. 21, 2016 (Jul. 21, 2016).
Anonymous: "Study to Evaluate the Efficacy, Safety, and Tolerability of Long-acting Intramuscular Cabotegravir and Rilpivirine for Maintenance of Virologic Suppression Following Switch From an Integrase Inhibitor in HIV-1 Infected Therapy Naïve Participants—Full Text View—ClinicalTrials.gov", (First posted: Oct. 19, 2016).
Anonymous: "Cabotegravir/rilpivirine—Wikipedia", Jun. 1, 2022 (Jun. 1, 2022), XP055927572.
EP office action dated Jun. 9, 2022.
U.S. National Library of Medicine ClinicalTrials.gov "A Phase IIb Study to Evaluate a Long-Acting Intramuscular Regimen for Maintenance of Virologic Suppression (Following Induction With an Oral Regimen of GSK1265744 and Abacavir/Lamivudine) in Human Immunodeficiency Virus Type 1 (HIV-1) Infected, Antiretroviral Therapy-Naive Adult Subjects" [Retrieved from Internet on Oct. 27, 2021] <URL: https://clinicaltrials.gov/study/NCT02120352.
Whitfield Thomas et al: "Profile of 1-16 cabotegravir and its potential in the treatment and prevention of HIV-1infection: evidence to date" HIV/AIDS, Auckland, N.Z, vol. 8, Jan. 1, 2016, pp. 157-164, ISSN: 1179-1373.
Margolis D et al: "THAB0206LB: A Cabotegravir plus rilpivirine as long-acting maintenance therapy: LATTE-2 week 48 results", Journal of the International AIDS Society, Biomed Central Ltd, London, UK, vol. 19, No. Suppl. 5, Jul. 22, 2016, p. 82, ISSN: 1758-2652.

(Continued)

*Primary Examiner* — Yih-Horng Shiao
(74) *Attorney, Agent, or Firm* — W. Brett Stauffer

(57) ABSTRACT

A method of treating HIV comprising intramuscular administration once every 4 weeks or less frequently of a combination of cabotegravir or a pharmaceutically acceptable salt thereof and rilpivirine or a pharmaceutically acceptable salt thereof, including the option of discontinuing administration of a first oral anti-retroviral regimen and intramuscularly administering, once four weeks or less often said combination of cabotegravir and rilpivirine.

30 Claims, 4 Drawing Sheets

(56) References Cited

OTHER PUBLICATIONS

Margolis DA et al: "Long-acting antiviral agents for HIV treatment", Current Opinion in HIV and AIDS, Lippincott Williams & Wilkins, US, vol. 10, No. 4, Jul. 1, 2015, pp. 246-252, ISSN: 1746-630X.

Third Party Observation PCT Nov. 21, 2019.

Murray, M. et al., 31st AIDS International Conference Jul. 18, 2016, Poster, col. 1, col. 2, Fig. 1.

ClinicalTrials.gov Identifier: NCT02120352: A Phase IIb Study to Evaluate a Long-Acting Intramuscular Regimen for Maintenance of Virologic Suppression. https://clinicaltrials.gov/ct2/show/NCT02120352. First posted Apr. 22, 2014. Available at https://clinicaltrials.gov/study/NCT02120352?term=NCT02120352&rank=1&tab=history&a=1#version-content-panel.

ClinicalTrials.gov Identifier: NCT02120352: A Phase IIb Study to Evaluate a Long-Acting Intramuscular Regimen for Maintenance of Virologic Suppression. https://clinicaltrials.gov/ct2/show/NCT02120352. Jun. 6, 2017. Available at https://clinicaltrials.gov/study/NCT02120352?term=NCT02120352&rank=1&tab=history&a=25#version-content-panel.

F.J. Palella et al., N. Engl. J. Med., (Mar. 26, 1998), vol. 338, pp. 853-860.

W. Spreen et al., "Pharmacokinetics, safety, and tolerability with repeat doses of GSK1265744 and rilpivirine (TMC278) long-acting nanosuspensions in healthy adults", JAcquirImmune Defic Syndr, (Dec. 15, 2014), vol. 67, No. 5, pp. 487-492.

S. Rusconi et al., "Long-acting agents for HIV infection: biological aspects, role in treatment and prevention, and patient's perspective," New Microbiologica, Apr. 2017, 40(2), pp. 75-79.

GSK R & D Event, Full Presentation, Nov. 3, 2015.

ViiV Press Release, "ViiV Healthcare announces positive headline results from a study of two drug injectable regimen for HIV maintenance therapy," Nov. 3, 2015.

ViiV Press Release, "ViiV Healthcare to progress collaboration with Janssen to develop the first long-acting two drug injectable regimen for treatment of HIV," Jan. 7, 2016.

Johnson & Johnson Press Release, "First Regimen Combining Long Acting Injectable Antiretrovirals; 32-Week LATTE 2 Study Results Presented at CROI," Feb. 24, 2016.

ClinicalTrials.gov Identifier: NCT02938520: Study to Evaluate the Efficacy, Safety, and Tolerability of Long-acting Intramuscular Cabotegravir and Rilpivirine for Maintenance of Virologic Suppression Following Switch From an Integrase Inhibitor in HIV-1 Infected Therapy Naive Participants. https://clinicaltrials.gov/study/NCT02938520. First posted Oct. 19, 2016. Available at https://clinicaltrials.gov/study/NCT02938520?tab=history&a=1#version-content-panel.

ClinicalTrials.gov Identifier: NCT02938520: Study to Evaluate the Efficacy, Safety, and Tolerability of Long-acting Intramuscular Cabotegravir and Rilpivirine for Maintenance of Virologic Suppression Following Switch From an Integrase Inhibitor in HIV-1 Infected Therapy Naive Participants. https://clinicaltrials.gov/study/NCT02938520. Feb. 15, 2024. Available at https://clinicaltrials.gov/study/NCT02938520?tab=history&a=39#version-content-panel.

ClinicalTrials.gov Identifier: NCT02951052: Study Evaluating the Efficacy, Safety, and Tolerability of Switching to Long-acting Cabotegravir Plus Long-acting Rilpivirine From Current Antiretroviral Regimen in Virologically Suppressed HIV-1-infected Adults. https://clinicaltrials.gov/study/NCT02951052. First posted Nov. 1, 2016. Available at https://clinicaltrials.gov/study/NCT02951052?term=nct02951052&rank=1&tab=history&a=1#version-content-panel.

ClinicalTrials.gov Identifier: NCT02951052: Study Evaluating the Efficacy, Safety, and Tolerability of Switching to Long-acting Cabotegravir Plus Long-acting Rilpivirine From Current Antiretroviral Regimen in Virologically Suppressed HIV-1-infected Adults. https://clinicaltrials.gov/study/NCT02951052. Feb. 14, 2024. Available at https://clinicaltrials.gov/study/NCT02951052?tab=history&a=66#version-content-panel.

Abstracts: CROI 2016 Conference on Retroviruses and Opportunistic Infections; Feb. 22-25, 2016; Boston, Massachusetts—p. 10 (31LB), D.A. Margolis et al., "Cabotegravir + Rilpivirine as Long-Acting Maintenance Therapy: LATTE-2 Week 32 Results".

D.A. Margolis et al.: Cabotegravir plus rilpivirine, once a day, after induction with cabotegravir plus nucleoside reverse transcriptase inhibitors in antiretroviral-naive adults with HIV-1 infection (LATTE): a randomised, phase 2b, dose-ranging trial. Lancet Infect. Dis 2015; 15:1145-1155. Jul. 20, 2015.

D.A. Margolis et al., "Cabotegravir + Rilpivirine as Long-Acting Maintenance Therapy: LATTE-2 Week 48 Results," International AIDS Conference (Jul. 18-22, 2016).

D.A. Margolis et al., "Cabotegravir + Rilpivirine as Long-Acting Maintenance Therapy: LATTE-2 Week 32 Results," 23rd Conference on Retroviruses and Opportunistic Infections, Feb. 22-25, 2016.

R.K.R. Rajoli et al., In Silico Dose Prediction for Long-Acting Rilpivirine and Cabotegravir Administration to Children and Adolescents. Clin Pharmacokinet (2018) 57:255-266, published online May 24, 2017.

Abstract Book, 21st International AIDS Conference, Jul. 28-22, 2016—p. 574, THPEB052, M. Murray et al., "Satisfaction, Tolerability, and Acceptability of Cabotegravir (CAB) + Rilpivirine (RPV) Long-Acting Therapy: LATTE-2 Results".

* cited by examiner

A

B

REGIMENS FOR TREATING HIV INFECTIONS AND AIDS

CROSS REFERENCE TO PRIOR APPLICATIONS

This Application is a Continuation of Ser. No. 18/145,065 filed 22 Dec. 2022 which is Pending; which is a Continuation of Ser. No. 16/631,868 filed 17 Jan. 2020 which Issued on 31 Jan. 2023 and is U.S. Pat. No. 11,564,921; which is a 371 National Stage of PCT/IB2018/055349 filed 18 Jul. 2018 which claims the priority of Provisional Application No. 62/535,302 filed 21 Jul. 2017, each of which is incorporated herein in its entirety.

FIELD OF THE INVENTION

The present invention provides methods and compositions for treating human immunodeficiency virus (HIV) or AIDS in a human subject.

BACKGROUND OF THE INVENTION

Human immunodeficiency virus ("HIV") infection and related diseases are a major public health problem worldwide. An estimated 37 million individuals were living with HIV worldwide in 2014. Global summary of the AIDS epidemic. World Health Organization. http://www.who.int/hiv/data/epi_core_july2015.png?ua=1. Accessed on Apr. 26, 2016.

Human immunodeficiency virus type 1 ("HIV-1") is a retrovirus which encodes three enzymes that are required for viral replication: reverse transcriptase, protease, and integrase. Although drugs targeting reverse transcriptase and protease are in wide use and have shown effectiveness, particularly when employed in combination, toxicity and development of resistant strains have limited their usefulness (Palella, et al., 1998 *N. Engl. J. Med.* 338:853-860; Richman, 2001 *Nature* 410:995-1001).

Antiretroviral therapy (ART) is intended to maximally suppress the HIV virus in an HIV infected human and to stop the progression of HIV disease. Further, a part of ART is the use of multiple drugs that act on different viral targets known as highly active antiretroviral therapy (HAART). Numerous clinical data sets have shown that an HIV viral load (RNA level) decreases following ART initiation and that the decrease in HIV viral load correlates with a reduced risk of AIDS progression and/or AIDS-related death. (Murray et al., *The use of plasma HIV RNA as a study endpoint in efficacy trials of antiretroviral drugs* 1999 *AIDS* 13 (7): 797-804; Marschner et al., *Use of changes in plasma levels of human immunodeficiency virus type 1 RNA to assess the clinical benefit of antiretroviral therapy,* 1998 *J Infect Dis.* 177 (1): 40-47; Thiebaut et al., *Clinical progression of HIV-1 infection according to the viral response during the first year of antiretroviral treatment,* 2000 *AIDS* 14 (8): 971-978.) In light of these findings, HIV viral load testing is an established technique for determining treatment response and, in particular, a decreased HIV viral load is an accepted marker of a positive treatment response. (HIV Surrogate Marker Collaborative Group, *Human immunodeficiency virus type 1 RNA level and CD4 count as prognostic markers and surrogate end points: a meta-analysis,* 2000 AIDS Res Hum Retroviruses, 16 (12): 1123-1133.) A statistically significant change in viral load is a three-fold change, which equates to a 0.5 log 10 copies/mL change. Depending on the study or assay used, viral suppression in general is defined as a viral load below the level of detection, which is an HIV RNA copy number of less than 20 to 75 copies per milliliter (c/mL). Viral suppression may be defined as an HIV RNA copy number less than 50 copies per milliliter (<50 c/mL). (Damond et al., *Human immunodeficiency virus type 1 (HIV-1) plasma load discrepancies between the Roche COBAS AMPLICOR HIV-1 MONITOR Version 1.5 and the Roche COBAS AmpliPrep/COBAS TaqMan HIV-1 assays,* 2007 *J Clin Microbiol.* 45 (10): 3436-3438.)

Treatment guidelines published by the United States Department of Health and Human Services provide that ART is recommended for all HIV-infected individuals (regardless of CD4 cell count) and achieving viral suppression requires the use of combination therapies (two or more drugs from at least two drug classes). (PANEL ON ANTIRETROVIRAL GUIDELINES FOR ADULTS AND ADOLESCENTS: GUIDELINES FOR THE USE OF ANTIRETROVIRAL AGENTS IN HIV-1-INFECTED ADULTS ADOLESCENTS. AND Department of Health and Human Services. Available at http://aidsinfo.nih.gov/ContentFiles/Adultand-AdolescentGL.pdf. Section accessed Apr. 19, 2017.) In fact, the standard course of care for a patient infected with HIV or diagnosed with AIDS is to treat them with a combination of three or more antiretroviral (ARV) agents ("combination antiretroviral therapy" (CART)). Frequently, this treatment uses two different antiretroviral agents each targeting HIV reverse transcriptase (a "backbone") and at least one additional antiretroviral agent (an "anchor") that is active against: an HIV protease inhibitor, an HIV non-nucleoside or non-nucleotide inhibitor of reverse transcriptase, an HIV nucleoside or nucleotide inhibitor of reverse transcriptase, an HIV integrase inhibitor, an HIV non-catalytic site (or allosteric) integrase inhibitor, or a combination thereof.

Advances in highly-active antiretroviral therapies (ARTs) have improved treatment efficacy for patients with HIV, enhancing patient survival and quality of life, but is a lifelong treatment (Blanc FX, Sok T, Laureillard D, et al. Earlier versus later start of antiretroviral therapy in HIV-infected adults with tuberculosis. *N Engl J Med* 2011; 365 (16): 1471-81.Walensky R P, Paltiel A D, Losina E, et al. The Survival Benefits of AIDS Treatment in the United States. *Journal of Infectious Diseases* 2006; 194 (1): 11-9). Patient non-compliance is a well known problem accompanying complex HIV treatment regimens and is a critical problem because it could lead to treatment failure and the emergence of multiple drug-resistant strains of HIV.

Long-acting injectable ART may provide some patients with a convenient and discreet approach to manage HIV infection. Margolis D A, Boffito M. Long-acting antiviral agents for HIV treatment. *Curr Opin HIV AIDS* 2015; 10 (4): 246-52. To date, no long-acting injectable regimen is available to patients with HIV.

WO2006/116764 discloses integrase strand transfer inhibitors (INSTI) useful in the treatment of HIV infection and AIDS. One of the compounds disclosed is cabotegravir ((3S,11aR)—N-[(2,4-difluorophenyl)methyl]-2,3,5,7,11, 11a-hexahydro-6-hydroxy-3-methyl-5,7-dioxo-oxazolo[3, 2-a]pyrido[1,2-d] pyrazine-8-carboxamide) a compound of formula (I), also referred to as compound (I), has proven antiviral activity against human immunodeficiency virus

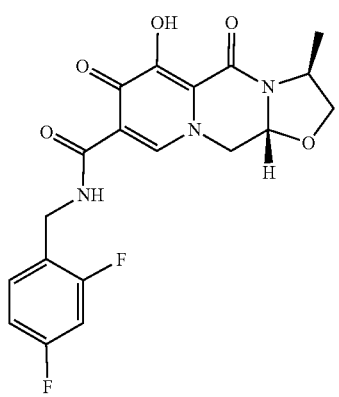

Oral administration of cabotegravir once daily has exhibited acceptable safety and tolerability profiles, a long half-life (40 hours), and few drug-drug interactions (Spreen W, Min S, Ford S L, et al. Pharmacokinetics, safety, and monotherapy antiviral activity of GSK1265744, an HIV integrase strand transfer inhibitor. *HIV Clin Trials* 2013; 14 (5): 192-203. Ford S L, Gould E, Chen S, et al. Lack of pharmacokinetic interaction between rilpivirine and integrase inhibitors dolutegravir and GSK1265744. *Antimicrob Agents Chemother* 2013; 57 (11): 5472-7. Spreen W R, Margolis D A, Pottage J C, Jr. Long-acting injectable antiretrovirals for HIV treatment and prevention. *Curr Opin HIV AIDS* 2013; 8 (6): 565-71).

Rilpivirine (EDURANT) is a potent non-nucleoside reverse transcriptase inhibitor (NNRTI) that is approved as a 25-mg once-daily oral medication for HIV-1 treatment and has the following structure:

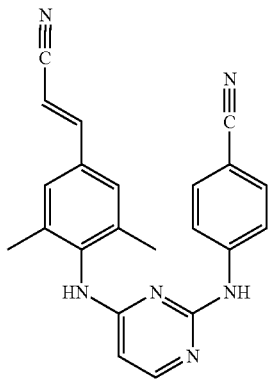 [SMILES: Cc1cc(/C=C/C#N)cc(C)c1Nc1ccnc(Nc2ccc(C#N)cc2)n1]

Long-acting injectable nanosuspension formulations of both cabotegravir and rilpivirine are in clinical development.

In the phase IIb LATTE trial (ClinicalTrials.gov identifier, NCT01641809), a two-drug regimen of once-daily oral formulations of cabotegravir and rilpivirine demonstrated durable viral suppression in subjects whose viral load was previously suppressed to <50 HIV-1 RNA copies per mL by treatment with cabotegravir and two nucleoside reverse transcriptase inhibitors (NRTIs), providing proof of principle for a two-drug maintenance regimen using an INSTI and NNRTI (Margolis D A, Brinson C C, Smith G H, et al. Cabotegravir plus rilpivirine, once a day, after induction with cabotegravir plus nucleoside reverse transcriptase inhibitors in antiretroviral-naive adults with HIV-1 infection (LATTE): a randomised, phase 2b, dose-ranging trial. *Lancet Infect Dis* 2015; 15 (10): 1145-55).

It would be desirable to have a regimen which requires less frequent administration, thus providing benefit to patients who have difficulty adhering to their antiviral medications.

The present invention provides methods and compositions for 4 week or longer dosing intervals, thereby addressing the problem of patient non-compliance.

SUMMARY OF THE INVENTION

The present invention provides methods and compositions for treating a subject infected with Human Immunodeficiency Virus with a long acting combination of cabotegravir or a pharmaceutically acceptable salt thereof and rilpivirine or a pharmaceutically acceptable salt thereof.

In a first aspect, the present invention provides a combination of cabotegravir or a pharmaceutically acceptable salt thereof and rilpivirine or a pharmaceutically acceptable salt thereof for use in the treatment of HIV by intramuscular administration once every 4 weeks or longer.

In a further aspect of the invention there is provided a pharmaceutical composition comprising a combination of cabotegravir or a pharmaceutically acceptable salt thereof and rilpivirine or a pharmaceutically acceptable salt thereof for use in the treatment of HIV by intramuscular administration once every 4 weeks or less frequently.

In a further aspect of the invention there is provided a method of treating HIV comprising intramuscular administration once every 4 weeks or longer of a combination of cabotegravir or a pharmaceutically acceptable salt thereof and rilpivirine or a pharmaceutically acceptable salt thereof.

DETAILED DESCRIPTION OF THE INVENTION

Definitions

Figure 1:
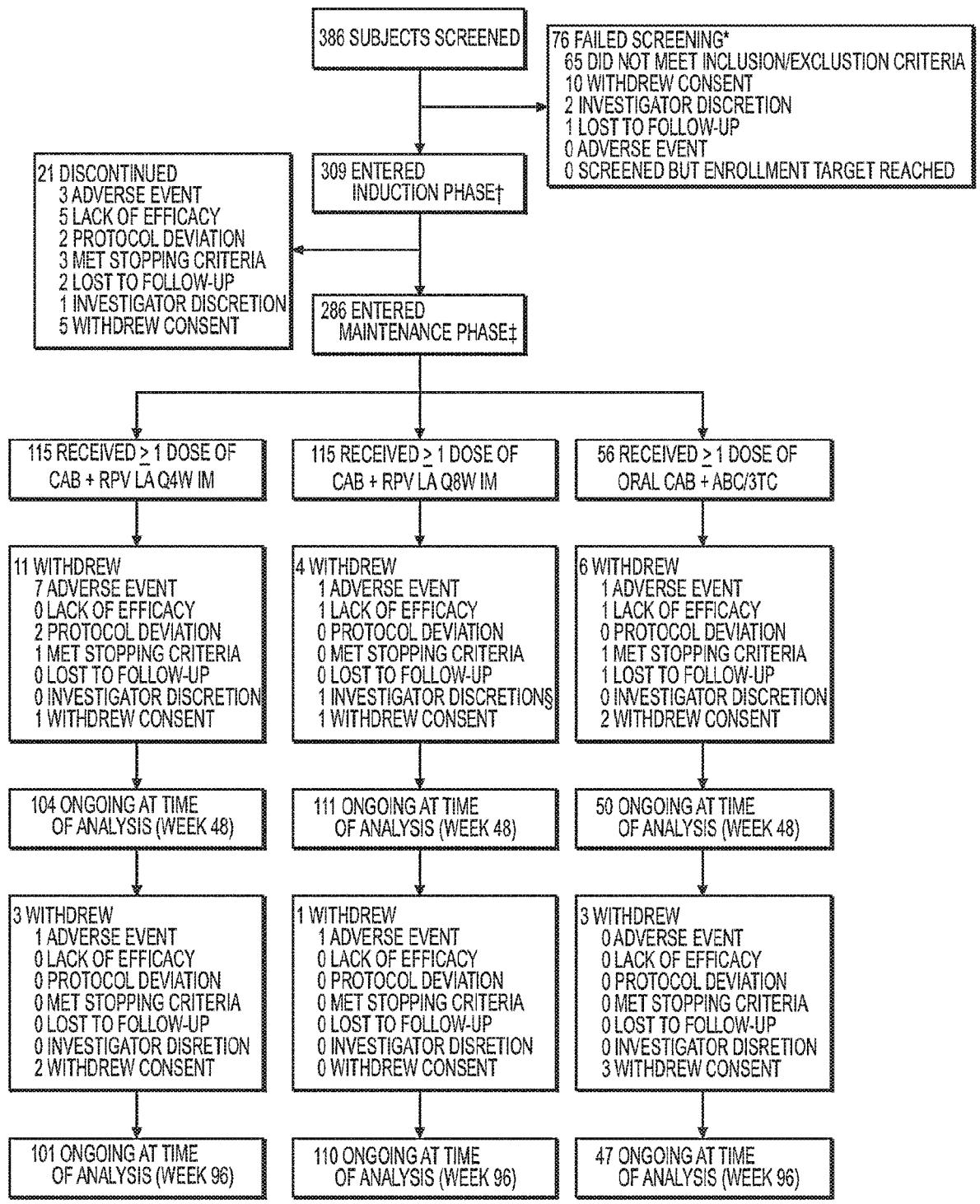
FIG. 1. LATTE-2 trial profile. IM, intramuscular; LA, long acting; PDVF, protocol-defined virologic failure; Q4W, every four weeks; Q8W, every eight weeks. *Multiple reasons for screening failure were reported for two subjects. †A total of 310 subjects were enrolled, but one subject withdrew consent after baseline visit procedures were performed and before study treatment was initiated. ‡Two subjects completed the induction period (and had Day 1 assessments) but did not enter the maintenance period and were not randomized (because of investigator discretion and lack of efficacy). § Subject experienced suspected PDVF at the time of withdrawal, which was subsequently confirmed.

HIV" or "human immunodeficiency virus" each means HIV-1 or HIV-2, or any mutant, group, clinical isolate, subtype, or clade thereof.

"Adult" as used herein means at least eighteen (18) years of age. The term "adult" may therefore be used to a reference a subject who is at least 18 years of age.

"Subject(s)" or "Human" or "Human subject(s)" or "Person(s)" herein are used to refer to a *Homo sapiens*.

Antiretroviral drug" or "ARV drug" as used herein means a molecule or compound classified as being a reverse transcriptase, protease, and/or integrase inhibitor "Pharmaceutically acceptable" as used herein means capable of administration to a subject without undesirable physiological effects. For example, "pharmaceutically acceptable salt thereof" encompasses solvates, polymorphs, and/or salts of the referenced compound.

"Sequential administration" or "adjacent administration" as used herein mean that at least two of the two or more referenced molecules, compounds, drugs, agents, etc., are not co-administered and are administered in succession (one after the other). In a particular embodiment of the invention, the two ARV drugs are sequentially administered within 1 hour. In a particular embodiment of the invention, the two ARV drugs are sequentially administered within 0.5 hour (i.e., 30 minutes). As used herein "within" is inclusive such that "within 1 hour," for example, includes 1 hour and times less than 1 hour.

"Simultaneous administration" as used herein means the two or more referenced molecules, compounds, drugs, agents, etc., are administered at the same time but not necessarily together in one composition. For example, in an embodiment of the invention two ARV drugs are administered at the same time but each is within a distinct (separate) pharmaceutical composition (i.e., not together). In an embodiment of the invention, "simultaneous" is defined as a time interval of 0 minutes.

The present invention demonstrates that subjects who were virologically suppressed on an oral cabotegravir-based therapy, switching to a long-acting combination of cabotegravir and rilpivirine maintained virologic suppression in 90% of patients overall through week 96 following four- or eight-week injectable administration at rates comparable to remaining on daily oral cabotegravir-based therapy thus representing a paradigm shift in the HIV treatment landscape by circumventing the burden of chronic daily dosing.

In one aspect of the present invention there is provided a method of treating HIV comprising intramuscular administration once every 4 weeks or longer of a combination of cabotegravir or a pharmaceutically acceptable salt thereof and rilpivirine or a pharmaceutically acceptable salt thereof.

In one embodiment, the treatment is every month or 4 weeks.

In one embodiment, the treatment is every 2 months or 8 weeks.

In a further aspect if the invention the subject is treatment naïve.

In a further aspect of the invention the subject is already receiving oral antiviral therapy.

In a further aspect of the invention, there is provided a method of modifying an anti-retroviral dosage regimen for a subject comprising
  discontinuing administration of a first oral anti-retroviral regimen to the subject; and intramuscularly administering to the subject, once every four weeks or longer a combination comprising
    rilpivirine, or a pharmaceutically acceptable salt thereof; and
    cabotegravir, or a pharmaceutically acceptable salt thereof;

The subject being switched from an oral antiviral regimen may particularly be on a three-drug regimen. In one embodiment, the first anti-retroviral regimen comprises
  cabotegravir; and
  two nucleoside reverse transcriptase inhibitors particularly abacavir and lamivudine In a further aspect of the invention, at the time of commencing treatment with the regimen of the present invention, as either a treatment-naïve subject or a subject being switched from an oral drug regimen, the subject exhibits a viral load of less than or equal to 50 copies of HIV-1 virus particles per mL of blood plasma (≤50c/mL).

In a further aspect of the invention, after administration, the subject is virologically suppressed. In one embodiment, virologically suppressed consists of a viral load no more than 50 copies of HIV RNA per milliliter (<50 c/mL) of the subject's plasma.

In a further embodiment, the subject preferably exhibits a viral load of less than or equal to 50 copies of HIV-1 virus particles per mL of blood plasma (≤50c/mL) after at least 96 weeks of the once every month or four weeks or longer administration of the dosage form.

In one embodiment, the treatment is every 4 weeks or one month, more particularly the treatment is every 4 weeks. In this embodiment, the dose is 400 mg cabotegravir and 600 mg rilpivirine, administered every four weeks. In a further embodiment the 400 mg cabotegravir and 600 mg rilpivirine, are administered separately in two 2-mL injections, every four weeks.

In one embodiment, the treatment is every 8 weeks or 2 months, more particularly the treatment is every 8 weeks. In this embodiment, the dose is 600 mg cabotegravir and 900 mg rilpivirine, administered every eight weeks. In a further embodiment, the 600 mg cabotegravir and 900 mg rilpivirine, are administered separately in two 3-mL injections, every 8 weeks.

Particular methods of treatment according to the present invention include

A method of modifying an anti-retroviral dosage regimen for a subject comprising
  discontinuing administration of a first oral anti-retroviral regimen to the subject; and intramuscularly administering to the subject, once every month or four weeks a combination comprising
    rilpivirine, or a pharmaceutically acceptable salt thereof; and
    cabotegravir, or a pharmaceutically acceptable salt thereof
wherein the subject exhibits a viral load of less than or equal to 50 copies of HIV-1 virus particles per mL of blood plasma (≤50c/mL) after at least 96 weeks of the once every month or four weeks administration of the dosage form.

A method of modifying an anti-retroviral dosage regimen for a subject comprising
  discontinuing administration of an first oral anti-retroviral regimen to the subject; and intramuscularly administering to the subject, once every 2 months or eight weeks a combination comprising
rilpivirine, or a pharmaceutically acceptable salt thereof; and
cabotegravir, or a pharmaceutically acceptable salt thereof
wherein the subject exhibits a viral load of less than or equal to 50 copies of HIV-1 virus particles per mL of blood plasma (≤50c/mL) after at least 96 weeks of the once every month or four weeks administration of the dosage form.

In a further aspect, the present invention provides a combination of cabotegravir or a pharmaceutically acceptable salt thereof and rilpivirine or a pharmaceutically acceptable salt thereof for use in the treatment of HIV by the above methods.

In a further aspect of the invention there is provided a pharmaceutical composition comprising a combination of cabotegravir or a pharmaceutically acceptable salt thereof and rilpivirine or a pharmaceutically acceptable salt thereof for use in the treatment of HIV by the above methods.

In one embodiment, the pharmaceutical composition comprises separate compositions of rilpivirine or a pharmaceutically acceptable salt thereof and cabotegravir or a pharmaceutically acceptable salt thereof. In one embodiment, the pharmaceutical composition of rilpivirine or a pharmaceutically acceptable salt thereof contains 300 mg (of rilpivirine as free compound) per mL. In one embodiment, the pharmaceutical composition of cabotegravir or a pharmaceutically acceptable salt thereof contains 200 mg (of cabotegravir as free compound) per mL. In one embodiment, both formulations are for intra-muscular administration.

In an embodiment of the invention, the subject is infected with Human Immunodeficiency Virus Type 1 (HIV-1).

The compounds of Formula (I) may be in the form of a salt.

Typically, the salts of the present invention are pharmaceutically acceptable salts. Salts encompassed within the term "pharmaceutically acceptable salts" refer to non-toxic salts of the compounds of this invention. For a review on suitable salts see Berge et al, J. Pharm. Sci. 1977, 66, 1-19.

While it is possible that, for use in therapy, the compound of the invention may be administered as the raw chemical, it is possible to present the compound of the invention as the active ingredient as a pharmaceutical composition. Such compositions can be prepared in a manner well known in the pharmaceutical art and comprise at least one active compound. Accordingly, the invention further provides pharmaceutical compositions comprising a combination of cabotegravir or a pharmaceutically acceptable salt thereof and rilpivirine or a pharmaceutically acceptable salt thereof and one or more pharmaceutically acceptable excipients. The excipient(s) must be acceptable in the sense of being compatible with the other ingredients of the composition and not deleterious to the recipient thereof. In accordance with another aspect of the invention there is also provided a process for the preparation of a pharmaceutical composition including the agent, or pharmaceutically acceptable salts thereof, with one or more pharmaceutically acceptable excipients. The pharmaceutical composition can be for use in the treatment and/or prophylaxis of any of the conditions described herein. The combination of cabotegravir or a pharmaceutically acceptable salt thereof and rilpivirine or a pharmaceutically acceptable salt thereof may be formulated together in one composition, or each of the active ingredients may be present in its own pharmaceutical composition.

Generally, the combination is administered in a pharmaceutically effective amount. The amount of the compound actually administered will typically be determined by a physician, in the light of the relevant circumstances, including the condition to be treated, the chosen route of administration, the actual compound-administered, the age, weight, and response of the individual patient, the severity of the patient's symptoms, and the like. Amounts suitable for the treatment of the present invention are detailed above.

The pharmaceutical composition is preferably suitable for parenteral, particularly intramuscular administration.

Pharmaceutical compositions adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

The active ingredients for use in the methods of the invention) may be employed in combination by administration simultaneously in a unitary pharmaceutical composition including both compounds. Alternatively, the combination may be simultaneously administered separately in separate pharmaceutical compositions, each including one of the compounds in a sequential manner wherein, for example, cabotegravir or a pharmaceutically acceptable salt thereof is administered first and rilpivirine or a pharmaceutically acceptable salt thereof second and vice versa. Suitably, both compounds are administered intramuscularly.

The combinations may be presented as a combination kit. By the term "combination kit" "or kit of parts" as used herein is meant the pharmaceutical composition or compositions that are used to administer the combination according to the invention. The combination kit can contain both compounds in a single pharmaceutical composition, or in separate pharmaceutical compositions either in a single package or in separate pharmaceutical compositions in separate packages.

The combination kit can also be provided by instruction, such as dosage and administration instructions. Such dosage and administration instructions can be of the kind that are provided to a doctor, for example by a drug product label, or they can be of the kind that are provided by a doctor, such as instructions to a patient.

When the combination is administered separately in a sequential manner wherein one is administered first and the other second or vice versa, such sequential administration may be close in time or remote in time. For example, administration of the other agent several minutes to several dozen minutes after the administration of the first agent. Conveniently they are administered simultaneously.

Methods

Cabotegravir and rilpivirine are antiretroviral drugs in development as long-acting injectable formulations. The LATTE-2 study evaluated long-acting cabotegravir+rilpivirine for maintenance of HIV-1 viral suppression through 96 weeks.

Methods

In this randomized, phase IIb, open-label study (Clinicaltrials.gov identifier, NCT02120352), HIV-1-infected, treatment-naive adults initially received oral cabotegravir 30 mg+abacavir/lamivudine 600/300 mg once daily. After 20 weeks, subjects with plasma HIV-1 RNA<50 copies per mL were randomized 2:2:1 to intramuscular long-acting cabotegravir+rilpivirine at four- or eight-week intervals or continued oral cabotegravir+abacavir/lamivudine. Endpoints included proportion of subjects with plasma HIV-1 RNA<50 copies per mL, protocol-defined virologic failures and safety events through 96 weeks for the maintenance-exposed population.

Results

Among 309 enrolled subjects, 286 were randomized into the maintenance period. Thirty-two weeks after randomization, viral suppression (HIV-1 RNA<50 copies per mL) was maintained in 91% (n=51) of subjects receiving oral cabotegravir+abacavir/lamivudine, 94% (n=108) in the four-week intramuscular group (+2.8% vs cabotegravir+abacavir/lamivudine, 95% CI, −5.8 to 11.5), and 95% (n=109) in the eight-week intramuscular group (+3.7% vs cabotegravir+abacavir/lamivudine; 95% CI, −4.8 to 12.2). Through Week 96, viral suppression was maintained in 84%, 87%, and 94% of subjects, respectively. Three subjects (1%) experienced protocol-defined virologic failure (eight-week intramuscular, n=2; oral, n=1). Injection-site reactions were mild (84%) or moderate (15%) in intensity and rarely resulted in discontinuation (<1%); injection-site pain was reported most frequently (96%). Serious adverse events were reported in 11% and 16% of subjects in the intramuscular and oral cabotegravir+abacavir/lamivudine groups, respectively; none were drug related.

Study Design

LATTE-2 is an ongoing phase IIb, randomized, multicenter, open-label, parallel-group study, consisting of a 20-week induction period, 96-week maintenance period, extension period, and long-term follow-up period. The study was conducted at 50 sites in the United States, Canada, Spain, France, and Germany. The first subject was screened in April 2014, and the last subject's Week 96 visit occurred in November 2016.

The study was performed in accordance with the principles of the Declaration of Helsinki. Written informed consent was obtained from all participants, and the protocol was approved by the institutional review board of each study site (ClinicalTrials.gov identifier, NCT02120352).

Study Participants

Subjects who were HIV-1 positive, were ≥18 years old, and had no more than ten days of previous ART treatment, with screening HIV-1 RNA≥1000 copies per mL and CD4+ T-cell counts ≥200 cells/mm$^3$, were eligible for inclusion. Key exclusion criteria included the presence of any major antiretroviral resistance-associated mutation, pregnancy, moderate or severe hepatic impairment, clinically relevant hepatitis, hepatitis B infection, laboratory values of clinical concern, creatinine clearance <50 mL/min, and a need for chronic anticoagulants.

Study Treatments

Eligible subjects received the induction period regimen of oral cabotegravir 30 mg+abacavir/lamivudine 600 mg/300 mg once daily for 20 weeks. Rilpivirine 25 mg once daily was added four weeks before randomization (Week −4 [Week 16 of the induction period]) and continued until the first injection visit (Day 1). Subjects who tolerated the induction period regimen and achieved plasma HIV-1 RNA<50 copies per mL at Week −4 were eligible to enter the maintenance period at Day 1. Eligible subjects were randomized 2:2:1 to receive intramuscular injections every four weeks (long-acting cabotegravir 400 mg+rilpivirine 600 mg; two 2-mL injections) or every eight weeks (long-acting cabotegravir 600 mg+rilpivirine 900 mg; two 3-mL injections), with a provision for a 14-day dosing window, or to continue receiving oral cabotegravir 30 mg+abacavir/lamivudine once daily for 96 weeks. Long-acting injectable formulations contained 200 mg per mL of cabotegravir and 300 mg per mL of rilpivirine for administration as two separate IM injections into the gluteus medius muscle at each dosing visit. Both four-week and eight-week dosing regimens had an initial loading dose of cabotegravir 800 mg (two 2-mL injections). Subject randomization, including stratification by HIV-1 RNA (≥ or <50 copies per mL) before Week-8 (ie, 12 weeks of induction treatment), utilized the validated randomization software, RandALL (Version 2.10; GlaxoSmithKline, Research Triangle Park, NC, USA).

Study Assessments

Planned analyses were conducted after all subjects had completed Weeks 32, 48, and 96 of the maintenance period (or discontinued earlier).

Primary endpoints included the proportion of subjects in the maintenance-exposed population (which consisted of randomized subjects who received at least one dose of study drug during the maintenance period) with HIV-1 RNA<50 copies per mL at maintenance Week 32 (using the US Food and Drug Administration [FDA] snapshot algorithm), proportion of subjects with protocol-defined virologic failures, and incidence and severity of adverse events and laboratory abnormalities.

Key secondary endpoints included the proportion of subjects with HIV-1 RNA<50 copies per mL at maintenance Week 48 and Week 96 (FDA snapshot algorithm), cabotegravir and rilpivirine plasma PK parameters during the maintenance period, and an assessment of regimen acceptability through subject-reported outcomes. Protocol-defined virologic failure following randomization was defined as having two consecutive plasma HIV-1 RNA measurements ≥200 copies per mL. Subjects who met the definition of protocol-defined virologic failure prior to receiving any cabotegravir+rilpivirine injections were discontinued from the study; those who had received one or more injections entered a 52-week long-term follow-up period.

Adverse events were graded according to the Division of AIDS Table for Grading the Severity of Adverse and Pediatric Events (2009).[17] Liver stopping criteria was met when alanine aminotransferase values met or exceeded the upper limit of normal by 8-fold, 5-fold for 14 days, or 3-fold with bilirubin ≥2× (>35% direct). Pharmacokinetic samples for cabotegravir and rilpivirine were collected at Day 1 and at Weeks 1, 4, 8, 12, 16, 20, 24, 25, 28, 32, 36, 40, 41, 44, and 48.

Treatment satisfaction was measured using the HIV Treatment Satisfaction Questionnaire (HIVTSQ). The HIVTSQ status version (HIVTSQ [s]) was completed by subjects at Weeks −16 and −4 of the induction period and at Day 1 (long-acting predose) and Weeks 8, 32, 48, and 96 of the maintenance period or at withdrawal.

Statistical Analyses

For the primary analysis, comparability in antiviral response (HIV-1 RNA<50 copies per mL) was assessed at Week 32 (and repeated at Week 48) using a Bayesian probability model. The primary decision criterion for efficacy was a posterior probability >90% that the intramuscular response rate was inferior to the oral response rate by no more than 10%. To incorporate prior beliefs, a beta (23, 2) distribution was assumed for the oral group response rate (mean, 92%; 2.5th/97.5th percentile, 78%/99%) and a non-informative prior distribution was assumed for the intramuscular response rate. Sample sizes of 45 subjects in the oral cabotegravir+abacavir/lamivudine group and 90 subjects each in the intramuscular groups were chosen to ensure a high probability that a two-drug long-acting regimen with poor response relative to oral cabotegravir+abacavir/lamivudine once daily would be identified. With the chosen number of subjects per treatment group, and assuming true response rates of 82% for long-acting cabotegravir+rilpivirine versus 92% for oral cabotegravir+abacavir/lamivudine, there was a low probability of falsely concluding that long-acting cabotegravir+rilpivirine was comparable with oral cabotegravir+abacavir/lamivudine (simulated probability=0.064). Each long-acting regimen was evaluated against the oral cabotegravir+abacavir/lamivudine group in the primary analysis; comparability in antiviral response rates between the two intramuscular regimens was assessed as a prespecified key secondary comparison. Data for the maintenance and induction plus maintenance periods combined, respectively, are summarized by randomized arm using the maintenance-exposed population, while data for the induction period and study population characteristics are summarized using the intent-to-treat exposed population (subjects who received at least one study dose during the induction period [Week-20 to Day 1]).

Change from baseline in CD4+ cell counts and subject-reported outcomes endpoints are summarized using observed data with no imputation for missing data. Laboratory abnormalities are presented as maintenance period treatment emergent, which refers to graded toxicities that developed or increased in intensity while on treatment in the maintenance period relative to the last recorded toxicity up to and including the date of the first dose of the maintenance period treatment.

Pharmacokinetic plasma concentrations following long-acting cabotegravir+rilpivirine administration are summarized using evaluable data that met sample collection window criteria, excluding samples affected by dosing errors (wrong dose) or oral bridging. Sampling windows for intramuscular dosing were set relative to the previous injection as follows: ±0.5 hours for two-hour postdose samples; ±one day for one-week postinjection visits; ±two days for predose samples in the four-week group, Weeks 4 and 8 cabotegravir samples in the eight-week group, and midcycle concentrations four weeks postinjection in the eight-week group; and ±four days for predose samples in the eight-week group (except for Weeks 4 and 8 cabotegravir samples, as described earlier).

Results

Study Subjects

Of 386 subjects screened, 309 were enrolled in the study (FIG. 1). A majority of subjects (91%) were male; the average age of subjects was 36.6 years. Nearly one-quarter of subjects (23%) had a CD4+ cell count ≤350 cells/mm$^3$, and 19% of subjects had baseline HIV-1 RNA≥100,000 copies per mL. There were 288 subjects (93%) who completed the 20-week induction period (intent-to-treat exposed). A total of 21 subjects (7%) discontinued treatment during the induction period (withdrew consent, n=5; lack of efficacy, n=5; adverse event, n=3; met predefined liver chemistry stopping criteria, n=3; protocol deviation, n=2; lost to follow-up, n=2; investigator discretion, n=1). A total of 286 subjects qualified for and entered the maintenance period. Subjects were randomized (2:2:1) to receive intramuscular injections of long-acting cabotegravir+rilpivirine every four weeks (n=115) or every eight weeks (n=115) or continue the oral cabotegravir+abacavir/lamivudine regimen (n=56; Table 1).

TABLE 1

Baseline Demographics and Disease Characteristics (Maintenance-Exposed Population)

| | Subjects* | | | |
|---|---|---|---|---|
| | Cabotegravir LA + rilpivirine LA Q4W IM (n = 115) | Cabotegravir LA + rilpivirine LA Q8W IM (n = 115) | Oral cabotegravir + abacavir/ lamivudine 30 mg (n = 56) | Total (n = 286) |
| Age, median (range) | 36 (19-62) | 35 (20-64) | 35 (19-57) | 35 (19-64) |
| Sex, male, n (%) | 109 (95) | 107 (93) | 46 (82) | 262 (92) |
| Ethnic origin, n (%) | | | | |
| White | 94 (82) | 93 (81) | 39 (70) | 226 (79) |
| African American/ African heritage | 12 (10) | 17 (15) | 15 (27) | 44 (15) |
| Other | 9 (8) | 5 (4) | 2 (4) | 16 (6) |
| Baseline HIV-1 RNA | | | | |
| Median (IQR) log$_{10}$ copies per mL | 4.46 (4.00-4.97) | 4.42 (4.05-4.80) | 4.29 (4.01-4.74) | 4.39 (4.03-4.83) |
| ≥100,000 copies per mL, n (%) | 28 (24) | 16 (14) | 7 (12) | 51 (18) |
| Baseline CD4+ cell count, median (IQR), cells/mm$^3$ | 499 (359-624) | 449 (343-618) | 518 (417-630) | 489 (359-624) |

TABLE 1-continued

Baseline Demographics and Disease Characteristics (Maintenance-Exposed Population)

| | Subjects* | | | |
|---|---|---|---|---|
| | Cabotegravir LA + rilpivirine LA Q4W IM (n = 115) | Cabotegravir LA + rilpivirine LA Q8W IM (n = 115) | Oral cabotegravir + abacavir/ lamivudine 30 mg (n = 56) | Total (n = 286) |
| Hepatitis C coinfection, n (%) | 5 (4) | 3 (3) | 2 (4) | 10 (3) |
| NRTI during induction, n (%) | | | | |
| Abacavir/lamivudine | 107 (93) | 107 (93) | 53 (95) | 267 (93) |
| Tenofovir/emtricitabine | 8 (7) | 8 (7) | 3 (5) | 19 (7) |

IM, intramuscular; IQR, interquartile range; LA, long acting; NRTI, nucleoside reverse transcriptase inhibitor; Q4W, every four weeks; Q8W, every eight weeks.
*Data are number of subjects (%) unless otherwise indicated.

In the maintenance period, 14 (12%), 5 (4%), and 9 (16%) subjects in the four-week, eight-week, and oral cabotegravir+abacavir/lamivudine groups, respectively, withdrew from the study (FIG. 1). The most common reasons for withdrawal during the maintenance period were adverse events (n=10 [3%]) and withdrawn consent (n=10 [3%]). Eight of the ten subjects who withdrew during the maintenance period because of adverse events were in the four-week group.

Efficacy

During the 20-week induction period, oral cabotegravir 30 mg+abacavir/lamivudine induced viral suppression (HIV-1 RNA<50 copies per mL) in 91% of subjects at Day 1 (Week 20 of induction period), with 90% of subjects achieving <50 copies per mL of HIV-1 RNA within the first eight weeks of treatment. One subject met the criteria for protocol-defined virologic failure (two consecutive plasma HIV-1 RNA measurements ≥200 copies per mL), as a result of poor medication compliance, without experiencing treatment-emergent resistance.

Following randomization, the proportion of subjects who achieved the primary efficacy endpoint (plasma HIV-1 RNA<50 copies per mL; FDA snapshot algorithm) at Week 32 was 94% for the four-week group, 95% for the eight-week group, and 91% for the oral cabotegravir+abacavir/lamivudine group (FIG. 2; Table S1), meeting prespecified criteria for claiming comparability (posterior probability of noninferiority >90%, Table S2).

TABLE S1

Snapshot Outcomes (HIV-1 RNA <50 copies per mL) in the Maintenance-Exposed Population

| | Subjects, n (%) | | |
|---|---|---|---|
| | Cabotegravir LA + rilpivirine LA Q4W IM (n = 115) | Cabotegravir LA + rilpivirine LA Q8W IM (n = 115) | Oral cabotegravir + abacavir/ lamivudine 30 mg (n = 56) |
| Week 32 | | | |
| Virologic response | 108 (94) | 109 (95) | 51 (91) |
| Difference vs oral cabotegravir, % (95% CI) | 2.8 (−5.8, 11.5) | 3.7 (−4.8, 12.2) | |
| Virologic nonresponse | 1 (<1) | 5 (4) | 2 (4) |
| Data in window not <50 copies per mL* | 1 (<1) | 3 (3) | 1 (2) |
| Discontinued for lack of efficacy | 0 | 1 (<1) | 1 (2) |
| Discontinued for other reason while not <50 copies per mL | 0 | 1 (<1) | 0 |
| No virologic data in window | 6 (5) | 1 (<1) | 3 (5) |
| Discontinued due to adverse event or death | 4 (3) | 0 | 1 (2) |
| Discontinued for other reasons | 2 (2) | 1 (<1) | 2 (4) |
| Week 48 | | | |
| Virologic response | 105 (91) | 106 (92) | 50 (89) |
| Difference vs oral cabotegravir, % (95% CI) | 2.0 (−7.6, 11.6) | 2.9 (−6.6, 12.4) | |
| Virologic nonresponse | 1 (<1) | 8 (7) | 1 (2) |
| Data in window not <50 copies per mL† | 1 (<1) | 6 (5) | 0 |

TABLE S1-continued

Snapshot Outcomes (HIV-1 RNA <50 copies per mL) in the Maintenance-Exposed Population

| | Subjects, n (%) | | |
|---|---|---|---|
| | Cabotegravir LA + rilpivirine LA Q4W IM (n = 115) | Cabotegravir LA + rilpivirine LA Q8W IM (n = 115) | Oral cabotegravir + abacavir/ lamivudine 30 mg (n = 56) |
| Discontinued for lack of efficacy | 0 | 1 (<1) | 1 (2) |
| Discontinued for other reason while not <50 copies per mL | 0 | 1 (<1) | 0 |
| No virologic data in window | 9 (8) | 1 (<1) | 5 (9) |
| Discontinued due to adverse event or death | 6 (5) | 0 | 2 (4) |
| Discontinued for other reasons | 3 (3) | 1 (<1) | 3 (5) |
| Week 96 | | | |
| Virologic response | 100 (87) | 108 (94) | 47 (84) |
| Difference vs oral cabotegravir, % (95% CI) | 3.0 (−8.4, 14.4) | 10.0 (−0.6, 20.5) | |
| Virologic nonresponse | 0 | 5 (4) | 1 (2) |
| Data in window not <50 copies per mL‡ | 0 | 2 (2) | 0 |
| Discontinued for lack of efficacy | 0 | 1 (<1) | 1 (2) |
| Discontinued for other reason while not <50 copies per mL | 0 | 2 (2) $^{II}$ | 0 |
| No virologic data in window | 15 (13) | 2 (2) | 8 (14) |
| Discontinued due to adverse event or death§ | 9 (8) | 1 (<1) | 2 (4) |
| Discontinued for other reasons | 5 (4) | 1 (<1) | 0 |
| Missing data during window but on study | 1 (<1) | 0 | 0 |

DILI, drug-induced liver injury; HCV, hepatitis C; IM, intramuscular; ISR, injection-site reaction; LA, long acting; Q4W, every four weeks; Q8W, every eight weeks.
*Week 32 HIV-1 RNA, Q4W: 70 copies per mL; oral cabotegravir: 243 copies per mL; Q8W: 53 copies per mL, 70 copies per mL, 91 copies per mL.
†Week 48 HIV-1 RNA, Q4W: 59 copies per mL; Q8W: 50 copies per mL, 57 copies per mL, 97 copies per mL, 110 copies per mL, 135 copies per mL, 463/205 copies per mL.
‡Week 96 HIV-1 RNA, 87 copies per mL, 118 copies per mL.
§Q8W: ISR/chills/body pain (n = 1); Q4W: HCV (n = 1), rash (n = 1), depressive reaction (n = 1), psychotic state (n = 1), Churg-Strauss vasculitis (n = 1), epilepsy (death; n = 1), mesenteric vein thrombosis (n = 1), QT prolongation/sinus tachycardia (n = 1), met liver stopping criteria (n = 1); Oral: acute HCV (n = 1), DILI (n = 1).
$^{II}$ Includes one subject who withdrew consent due to intolerance of injections.

TABLE S2

Probabilities of Noninferiority From Primary Bayesian Analysis*

| Comparison of treatment groups† | Estimated posterior probability given Week 32 response rates, %† | Estimated posterior probability given Week 48 response rates, %† |
|---|---|---|
| Q4W vs oral | 99.9 | 99.4 |
| Q8W vs oral | 100 | 99.7 |
| Q8W vs Q4W | 99.9 | 99.8 |

IM, intramuscular; P, probability; Q4W, every four weeks; Q8W, every eight weeks.
*Posterior probability >90% was the prespecified margin to conclude comparability in response rates (HIV-1 RNA concentration <50 copies per mL by FDA snapshot algorithm). For comparisons between IM and oral treatment groups, comparability criterion was $P_{IM}$ > $P_{oral}$ − 10%; for comparison between the Q8W and Q4W treatment groups, comparability criterion was $|P_{Q8W} − P_{Q4W}| < 10\%$.
†Rates assumed to follow noninformative beta (1, 1) prior distributions for $P_{Q8W}$ and $P_{Q8W}$ and informative beta (23, 2) prior distribution for $P_{oral}$.

Treatment differences at Week 32 for each group receiving long-acting injections compared with daily oral cabotegravir+abacavir/lamivudine were 3.7% (95% CI, −4.8 to 12.2) for the four-week group and 2.8% (95% CI, −5.8 to 11.5) for the eight-week group. At Week 48, comparability between regimens was confirmed (Table S2), with virologic suppression achieved in 91%, 92%, and 89% of subjects in the four-week, eight-week, and oral cabotegravir+abacavir/lamivudine groups, respectively, (FIG. 2; Table S1).

Figure 2:
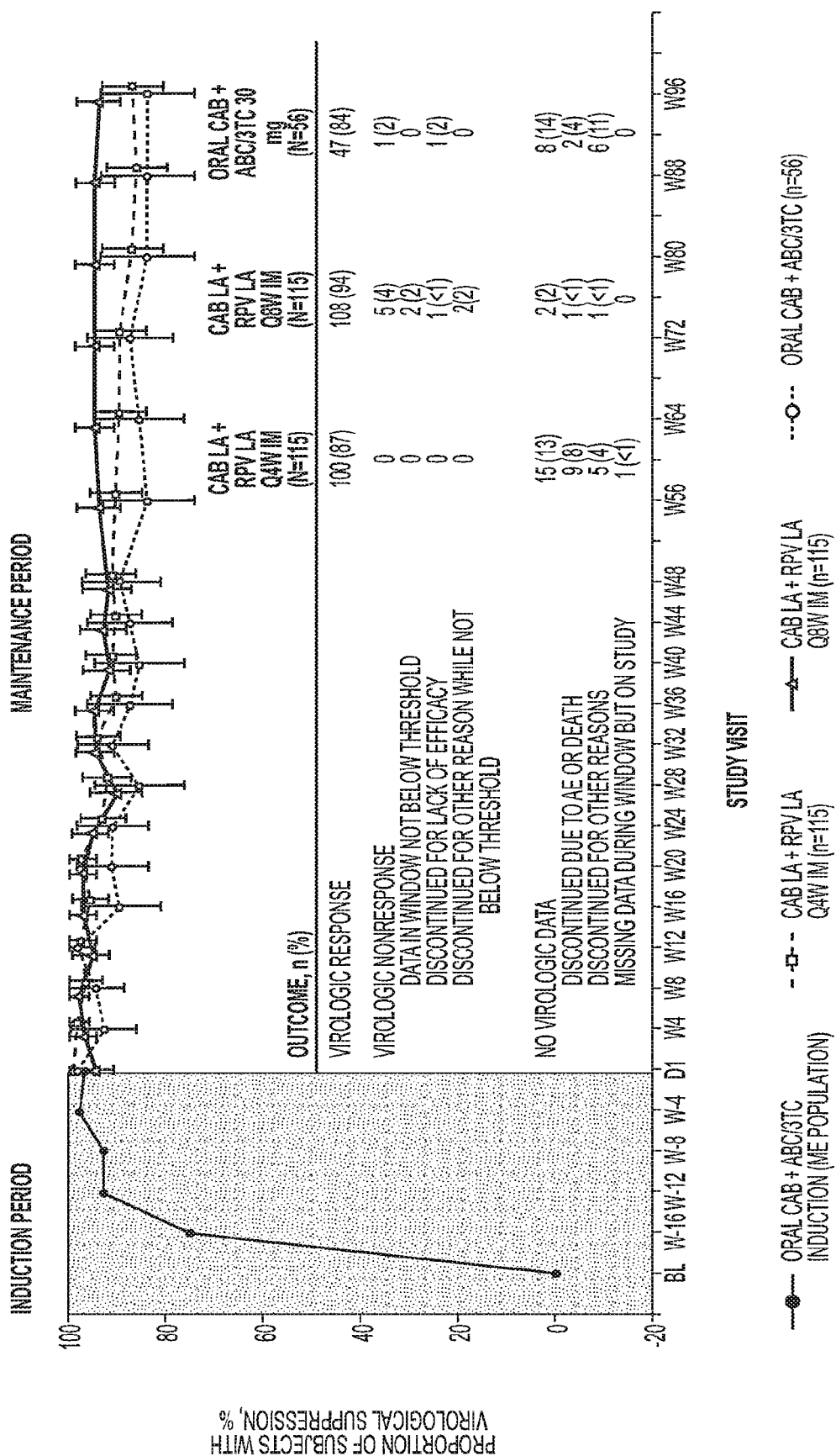
FIG. 2. Proportion of subjects with HIV-1 RNA concentration <50 copies per mL (FDA snapshot algorithm) by visit in the maintenance-exposed population and snapshot outcomes at Week 48. AE, adverse event; BL, baseline; D, day; FDA, US Food and Drug Administration; IM, intramuscular; ME, maintenance-exposed; LA, long acting; PDVF, protocol-defined virologic failure; Q4W, every four weeks; Q8W, every eight weeks; W, week.

Through 96 weeks of maintenance treatment, 87%, 94% and 84% of subjects in the four-week, eight-week and oral cabotegravir+abacavir/lamivudine groups, respectively, maintained virologic suppression, respectively (FIG. 2; Table S1). Virologic nonresponse, as defined by the FDA snapshot algorithm, occurred in six subjects (eight-week group, n=5; oral cabotegravir+abacavir/lamivudine group, n=1; FIG. 2). Through 96 weeks, no subjects in the four-week group failed for virologic reasons. In comparison, at Week 48, ten subjects met virologic nonresponse criteria (four-week group, n=1; eight-week group, n=8; oral cabotegravir+abacavir/lamivudine group, n=1). For the eight-week group, four subjects with virologic nonresponse at Week 48 (HIV-1 RNA>50 copies per mL) were resuppressed with HIV-1 RNA <50 copies per mL at Week 96 without a change in therapy. Of the five eight-week subjects with virologic nonresponse at Week 96, two had HIV-1 RNA≥50 copies per mL at Week 96 (one of which had HIV-1≥50 copies per mL at Week 48), one discontinued due to protocol-defined virologic failure at Week 4, one withdrew consent due to intolerance of injections at Week 8, and one withdrew due to investigator discretion at Week 48 while not suppressed (and subsequently confirmed as a protocol-defined virologic failure). One of the two subjects with HIV-1 RNA>50 copies per mL at Week 96 remained on the study and had HIV-1 levels <50 copies per mL at the next scheduled visit. The four-week group subject with virologic nonresponse at Week 48 (HIV-1 RNA, 59 copies per mL) remained on the study beyond Week 48 and had subsequent viral resuppression with HIV-1<50 copies per mL at Week 96. The virologic nonresponder in the oral cabotegravir+abacavir/lamivudine group discontinued as a result of protocol-defined virologic failure at Week 8.

Three randomized subjects (eight-week group, n=2 (Week 4 and Week 48); oral cabotegravir+abacavir/lamivudine group, n=1 (Week 8) met the criteria for protocol-defined virologic failure through Week 96. Viral genotyping analysis for the subject in the oral cabotegravir+abacavir/lamivudine group demonstrated no treatment-emergent resistance mutations in the genes encoding viral reverse transcriptase, protease, or integrase. Of the two subjects in the eight-week group, a mixture emerged for one at integrase codon 269 (R269R/G), which did not decrease cabotegravir susceptibility. The second subject harbored virus with treatment-emergent reverse transcriptase mutations K103N, E138G, and K238T, with phenotypic resistance to efavirenz, rilpivirine, and nevirapine, and an integrase mutation Q148R, with phenotypic resistance to raltegravir, elvitegravir, and cabotegravir, while remaining sensitive to dolutegravir.

CD4+ cell counts increased from the beginning of the induction period by median (interquartile range) of 226 (145-393) cells/mm$^3$, 239 (111-359) cells/mm$^3$, and 317 (214-505) cells/mm$^3$ in subjects in the four-week (n=100), eight-week (n=109), and oral cabotegravir+abacavir/lamivudine (n=47) groups, respectively, at Week 96 of the maintenance period.

Safety

Adverse Events

During the induction and maintenance period, in the maintenance-exposed population, total adverse events of any grade and attribution occurred in 100%, 100%, and 96% of subjects in the four-week, eight-week, and oral cabotegravir+abacavir/lamivudine groups, respectively (Table 2).

TABLE 2

Summary of Total Adverse Events and Treatment-Related Adverse Events Through Week 96 in the Safety Maintenance Population*

| | Subjects, n (%) | | | | | |
|---|---|---|---|---|---|---|
| | Cabotegravir LA + rilpivirine LA Q4W IM (n = 115) | | Cabotegravir LA + rilpivirine LA Q8W IM (n = 115) | | Oral cabotegravir + abacavir/lamivudine 30 mg (n = 56) | |
| | Total adverse events | | | | | |
| | Grade 1-4$^\dagger$ | Grade 3-4$^\S$ | Grade 1-4$^\dagger$ | Grade 3-4$^\S$ | Grade 1-4$^\dagger$ | Grade 3-4$^\S$ |
| Any event | 115 (100) | 21 (18) | 115 (100) | 24 (21) | 54 (96) | 7 (13) |
| Injection-site pain | 112 (97) | 6 (5) | 110 (96) | 8 (7) | 0 | 0 |
| Nasopharyngitis | 39 (34) | 0 | 35 (30) | 0 | 22 (39) | 0 |
| Injection-site nodule | 36 (31) | 1 (<1) | 29 (25) | 1 (<1) | 0 | 0 |
| Injection-site swelling | 34 (30) | 0 | 29 (25) | 1 (<1) | 0 | 0 |
| Diarrhoea | 32 (28) | 0 | 27 (23) | 0 | 11 (20) | 0 |
| Injection-site pruritus | 33 (29) | 0 | 25 (22) | 0 | 0 | 0 |
| Headache | 27 (23) | 0 | 29 (25) | 0 | 14 (25) | 1 (2) |
| Injection-site induration | 25 (22) | 0 | 29 (25) | 1 (<1) | 0 | 0 |
| Injection-site warmth | 21 (18) | 0 | 23 (20) | 1 (<1) | 0 | 0 |
| Upper respiratory tract infection | 13 (11) | 0 | 23 (20) | 0 | 7 (13) | 0 |
| Injection-site bruising | 14 (12) | 0 | 20 (17) | 0 | 0 | 0 |
| Nausea | 18 (16) | 0 | 16 (14) | 0 | 9 (16) | 0 |
| Injection-site erythema | 19 (17) | 0 | 13 (11) | 1 (<1) | 0 | 0 |
| Pyrexia | 16 (14) | 0 | 16 (14) | 0 | 3 (5) | 0 |
| Gastroenteritis | 15 (13) | 0 | 14 (12) | 0 | 6 (11) | 1 (2) |
| Fatigue | 14 (12) | 0 | 14 (12) | 0 | 4 (7) | 0 |
| Syphilis | 11 (10) | 0 | 17 (15) | 0 | 6 (11) | 0 |
| Back pain | 13 (11) | 0 | 15 (13) | 0 | 10 (18) | 0 |
| Insomnia | 13 (11) | 0 | 12 (10) | 0 | 4 (7) | 0 |
| Bronchitis | 12 (10) | 1 (<1) | 12 (10) | 0 | 6 (11) | 0 |
| Cough | 13 (11) | 0 | 11 (10) | 0 | 7 (13) | 0 |
| Influenza | 16 (14) | 0 | 6 (5) | 0 | 2 (4) | 0 |
| Arthralgia | 10 (9) | 0 | 12 (10) | 0 | 4 (7) | 0 |
| Anogenital warts | 11 (10) | 0 | 9 (8) | 0 | 2 (4) | 0 |
| Pharyngitis | 8 (7) | 0 | 12 (10) | 0 | 5 (9) | 0 |
| Respiratory tract infection | 11 (10) | 0 | 6 (5) | 0 | 6 (11) | 0 |
| Asthenia | 10 (9) | 0 | 7 (6) | 0 | 9 (16) | 0 |
| Treatment-related adverse events | | | | | | |
| | Grade 1-4$^\ddagger$ | Grade 3-4$^\S$ | Grade 1-4$^\ddagger$ | Grade 3-4$^\S$ | Grade 1-4$^\ddagger$ | Grade 3-4$^\S$ |
| Any event | 113 (98) | 10 (9) | 110 (96) | 10 (9) | 21 (38) | 1 (2) |
| Injection-site pain | 112 (97) | 6 (5) | 109 (95) | 8 (7) | 0 | 0 |
| Injection-site nodule | 35 (30) | 1 (<1) | 29 (25) | 1 (<1) | 0 | 0 |
| Injection-site swelling | 34 (30) | 0 | 29 (25) | 1 (<1) | 0 | 0 |
| Injection-site pruritus | 33 (29) | 0 | 24 (21) | 0 | 0 | 0 |

TABLE 2-continued

Summary of Total Adverse Events and Treatment-Related Adverse
Events Through Week 96 in the Safety Maintenance Population*

| Injection site induration | 25 (22) | 0 | 28 (24) | 1 (<1) | 0 | 0 |
|---|---|---|---|---|---|---|
| Injection-site warmth | 21 (18) | 0 | 22 (19) | 1 (<1) | 0 | 0 |
| Injection-site bruising | 14 (12) | 0 | 19 (17) | 0 | 0 | 0 |
| Injection-site erythema | 19 (17) | 0 | 12 (10) | 1 (<1) | 0 | 0 |
| Nausea | 12 (10) | 0 | 8 (7) | 0 | 5 (9) | 0 |
| Headache | 7 (6) | 0 | 6 (5) | 0 | 4 (7) | 0 |
| Pyrexia | 7 (6) | 0 | 5 (4) | 0 | 0 | 0 |
| Injection site discolouration | 6 (5) | 0 | 3 (3) | 0 | 0 | 0 |
| Dyspepsia | 6 (5) | 0 | 1 (<1) | 0 | 1 (2) | 0 |
| Asthenia | 3 (3) | 0 | 2 (2) | 0 | 3 (5) | 0 |

IM, intramuscular; LA, long acting; Q4W, every four weeks; Q8W, every eight weeks.
*Includes all post-baseline induction period and maintenance period adverse events, as well as long-term follow-up period adverse events for subjects withdrawing from intramuscular dosing that occurred within 35/63 days (Q4W/Q8W) of the last maintenance period IM injection until up to and including the start date of the long-term follow-up period oral highly active antiretroviral treatment.
†≥10% in any treatment group.
‡≥5% in any treatment group.
§Includes only events listed in the grade 1-4 column; other grade 3-4 events that did not meet the 5% or 10% cut-off for the grade 1-4 column are not shown.

Injection-site pain, the most common injection-site reaction (ISR), was the most frequently reported adverse event in the intramuscular groups (four-week group, 97%; eight-week group, 96%). Most ISRs were mild (84%) or moderate (15%) in intensity, with median symptom duration of three days (Table S3).

TABLE S3

Summary of Injection-Site Reactions in Q4W and Q8W
Cabotegravir Plus Rilpivirine IM Treatment Groups

| | Subjects, n (%) | | |
|---|---|---|---|
| | Cabotegravir LA + rilpivirine LA Q4W IM (n = 115) | Cabotegravir LA + rilpivirine LA Q8W IM (n = 115) | Cabotegravir LA + rilpivirine LA IM subtotal (n = 230) |
| Number of injections | 5419 | 3160 | 8579 |
| Number of ISR events | 2435 | 1925 | 4360 |
| Grades, n (%) | | | |
| Grade 1 | 2105 (86) | 1543 (80) | 3648 (84) |
| Grade 2 | 314 (13) | 359 (19) | 673 (15) |
| Grade 3 | 14 (<1) | 16 (<1) | 30 (<1) |
| Grade 4 | 0 | 0 | 0 |
| Duration, days | | | |
| ≤7 | 2172 (89) | 1718 (89) | 3890 (89) |
| 8-14 | 162 (7) | 133 (7) | 295 (7) |
| >14 | 78 (3) | 51 (3) | 129 (3) |
| Median (range) | 3.0 (1-138) | 3.0 (1-176) | 3.0 (1-176) |

IM, intramuscular; ISR, injection-site reaction; LA, long acting; Q4W, every four weeks; Q8W, every eight weeks.

The most commonly reported non-ISR adverse events were nasopharyngitis (four-week group, 34%; eight-week group, 30%; oral cabotegravir+abacavir/lamivudine groups, 39%), diarrhea (four-week group, 28%; eight-week group, 23%; oral cabotegravir+abacavir/lamivudine group, 20%), and headache (four-week group, 23%; eight-week group, 25%; oral cabotegravir+abacavir/lamivudine group, 25%). Serious adverse events occurred in 11% of subjects in each of the intramuscular treatment groups and 16% of subjects in the oral cabotegravir+abacavir/lamivudine group, only one of which was drug related (migraine, which occurred in the initial oral induction period of the study). During the maintenance period, serious adverse events occurred in 10% of subjects in each intramuscular group compared with 13% in the oral cabotegravir+abacavir/lamivudine group. However, none was considered to be related to study treatment. Eleven subjects (4%) developed an adverse event during the maintenance period, which led to withdrawal: eight subjects (7%) in the four-week group, two subjects in the eight-week group (2%), and one subject in the oral cabotegravir+abacavir/lamivudine group (2%). Two subjects (both in the eight-week group) had ISRs leading to withdrawal within eight weeks of initiating dosing. Two deaths occurred during the study: one resulted from a motor vehicle accident that occurred in the initial oral induction period of the study, and the second occurred after an epileptic seizure in a subject in the four-week intramuscular treatment group who had received 48 weeks of cabotegravir and 32 weeks of rilpivirine treatment. Neither death was considered to be related to study treatment.

Laboratory Abnormalities

Grade ≥3 maintenance period treatment-emergent laboratory abnormalities occurred in 29% of subjects in the four-week group, 19% of subjects in the eight-week group, and 21% of subjects in the oral cabotegravir+abacavir/lamivudine group. Grade ≥3 maintenance period treatment-emergent ALT elevations occurred in 3% of subjects in both four-week and eight-week intramuscular dosing, and in 5% of subjects receiving oral cabotegravir+abacavir/lamivudine. Among subjects meeting pre-defined liver stopping criteria, possible drug-induced liver injury occurred in two subjects (both treated with oral cabotegravir+abacavir/lamivudine; one during the induction period [before randomization] and one during the maintenance period). In both cases, liver chemistry abnormalities resolved following treatment discontinuation, and the subjects remained clinically asymptomatic.

Pharmacokinetics

Figure 3:
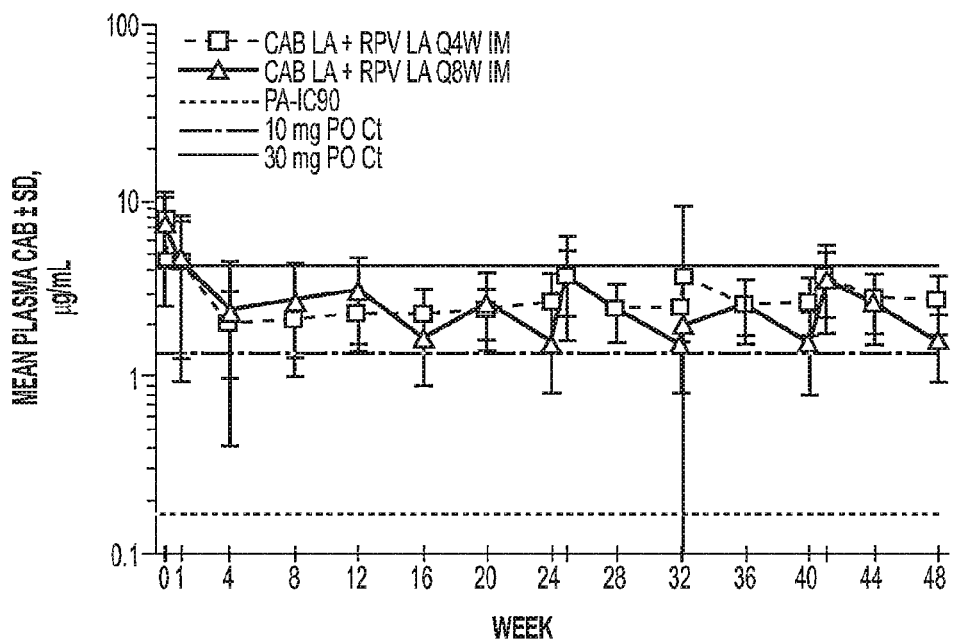
FIG. 3. Mean concentration-time profiles following Q4W and Q8W administration of (A) cabotegravir LA and (B) rilpivirine LA through Week 48. Ct, concentration at the end of dosing interval; IM, intramuscular; LA, long acting; PA-IC90, protein-adjusted 90% inhibitory concentration; PO, orally; Q4W, every four weeks; Q8W, every eight weeks; SD, standard deviation.
Figure 3:
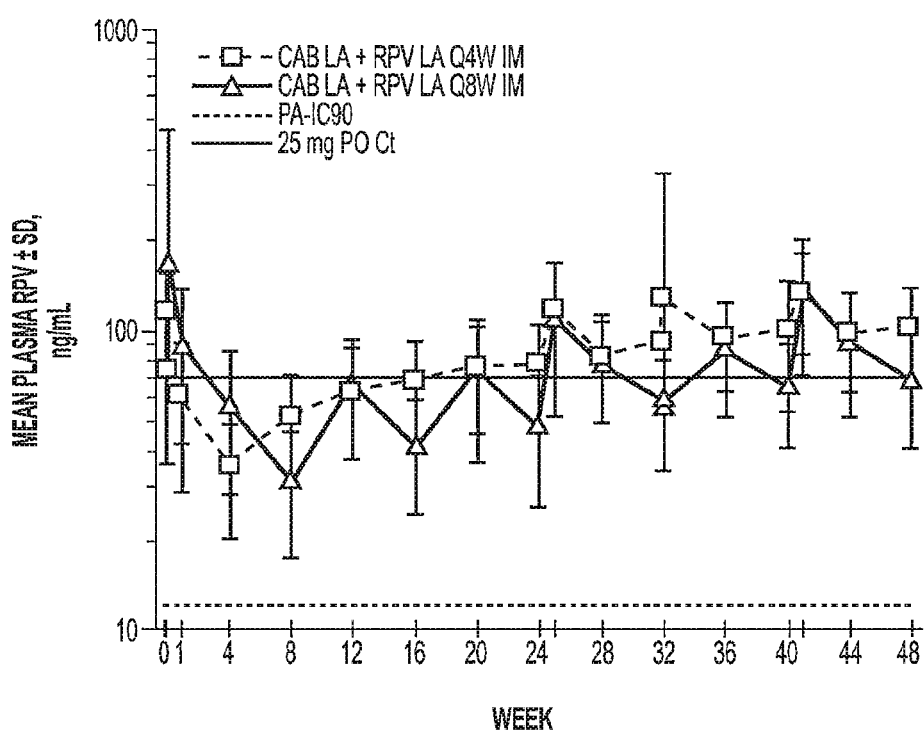

At Week 48, cabotegravir geometric mean trough concentrations ($C_0$; 95% confidence interval [CI]) were 2.58 µg/mL (2.4 to 2.8 µg/mL), 1.46 µg/ml (1.3 to 1.6 µg/mL), and 4:47 µg/mL (3.9 to 5.2 µg/mL) for the four-week, eight-week, and oral cabotegravir+abacavir/lamivudine groups, respectively, which were 16-fold, 9-fold, and 27-fold greater than the in vitro protein-adjusted 90% inhibitory concentration (PA-IC90) of 0.166 µg/mL against wild-type HIV-1. For rilpivirine, Week 48 geometric mean $C_0$ (95% CI) values were 94.64 ng/ml (866 to 103.4 ng/ml) and 64:48 ng/mL (60.0 to 69:3 ng/ml) for the four-week and eight-week regimens, respectively (FIG. 3), which were 8-fold and 5-fold greater than in vitro PA-IC90 of 12 ng/ml against wild-type HIV-1. Accumulation of rilpivirine was observed through 48 weeks of dosing, with the lowest rilpivirine trough concentrations observed after initial intramuscular injections in both arms (FIG. 3). No relationship was observed between cabotegravir concentrations and virologic nonresponse at Week 48. In seven of the nine subjects in the eight-week regimen with virologic nonresponse at Week 48 (FDA snapshot algorithm), rilpivirine trough concentrations at Week 48 (or last available trough concentration before Week 48) were in the lowest 25th quartile among all rilpivirine samples, whereas cabotegravir trough concentrations were distributed throughout the quartile ranges. Of the two subjects in the eight-week regimen with protocol-defined virologic failure during the maintenance period through Week 48, one subject had nonquantifiable rilpivirine concentration four weeks post injection (indicative of accidental partial intravenous administration) without treatment-emergent resistance, and there was no clear correlation between cabotegravir or rilpivirine concentrations at the time of viral rebound with the other subject. Sparse PK sampling obtained after Week 48 and through Week 96 was not assayed as a matter of routine and therefore is not reported.

Subject-Reported Health Outcomes

Figure 4:
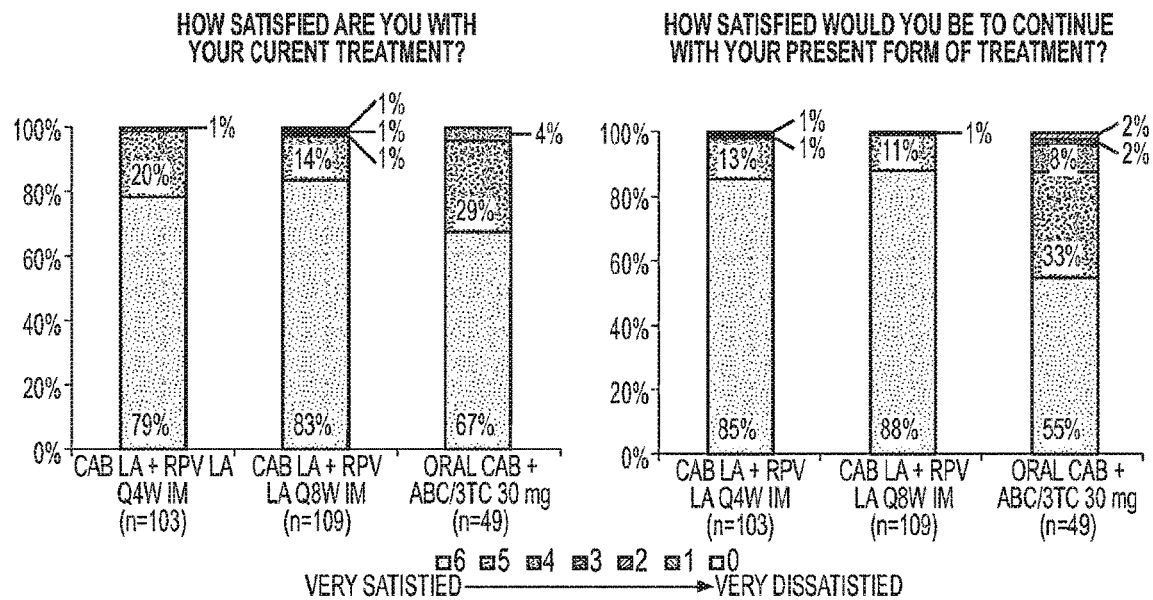
FIG. 4. Summary of subject-reported outcomes at (A) Week 48 (maintenance treatment) and (B) Week 96. The data are based on the observed case data set of subjects who completed questionnaires at Week 48 and Week 96 (HIV Treatment Satisfaction Questionnaire status version). IM, intramuscular; LA, long acting; Q4W, every four weeks; Q8W, every eight weeks.
Figure 4:
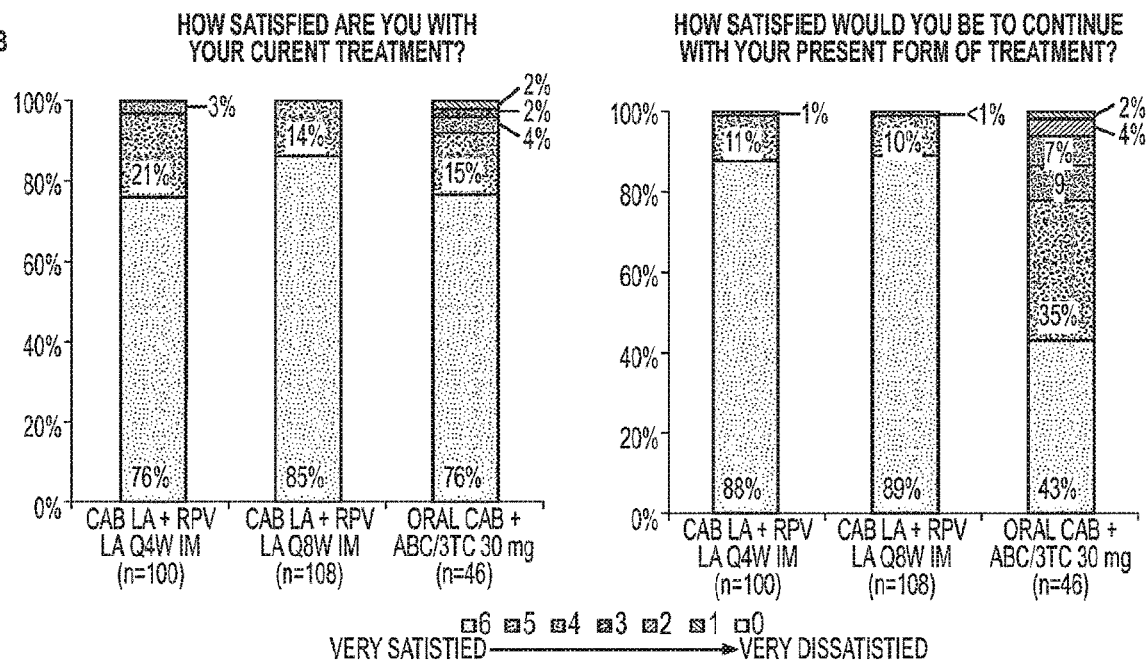

High levels of treatment satisfaction were observed across all treatment groups (FIG. 4). At Week 96, subjects reported very high levels of satisfaction with all three arms, four-week, eight-week, and oral cabotegravir+abacavir/lamivudine, via the HIVTSQ(s), with 95% of these subjects selecting a score of 5 or 6 on a 6-point satisfaction scale. A similar percentage of subjects in each of the intramuscular groups (≥99%) reported they would be highly satisfied to continue their current long-acting regimen, while a lower percentage, 78%, would elect to continue on oral dosing. Subjects who discontinued for any reason before Week 96 did not complete the questionnaire at this time point, introducing a small degree of selection bias in these results.

DISCUSSION

LATTE-2 was the first study to analyze the efficacy and safety of a fully injectable two-drug long-acting ART regimen in subjects with HIV-1 infection. Both the long-acting injectable four-week and eight-week regimens maintained virologic suppression at rates comparable to oral daily three-drug ART, with two protocol-defined virologic failures occurring among the 230 subjects who received long-acting therapy during the 96-week maintenance period. The long-acting cabotegravir+rilpivirine regimens were generally well tolerated, with no drug-related serious adverse events and few adverse event-related withdrawals. While injection-site reactions were common, they were transient in nature, mild or moderate in severity, and did not appear to compromise high levels of subject-reported satisfaction. The long-term acceptability of administering chronic IM injections to patients was also demonstrated in LATTE-2, with very few withdrawals resulting from injection-site reactions, two subjects (<1%) through 96 weeks.

Treatment with the four-week and eight-week regimens maintained virologic suppression in 87% and 94% of subjects, respectively, compared with 84% of subjects treated with oral cabotegravir+abacavir/lamivudine. These proportions are consistent with multiple other studies examining efficacy of oral switch regimens in subjects with viral suppression on an initial regimen.[18-20] Few virologic nonresponders, as determined by the rigorous FDA snapshot algorithm, were observed with either long-acting regimen in the LATTE-2 study, with a higher rate of nonresponse observed in the eight-week group (n=5 [4%]) than in the four-week group (n=0). Only two subjects in the eight-week group, and none in the four-week group, met the criteria for protocol-defined virologic failure. One participant had emergence of well-described NNRTI and INSTI mutations that conferred reduced susceptibility. No NNRTI mutations were observed in the second participant, who had undetectable rilpivirine concentrations, and a mixture emerged at an integrase codon not associated with INSTI resistance[21] with no change in cabotegravir susceptibility. The efficacy profile and lack of virologic failures in the four-week regimen has led to the selection of an optimized four-week dosing regimen in the ongoing phase III clinical program, while the eight-week regimen remains under longer-term evaluation within the LATTE-2 study.

One of the potential challenges of injectable long-acting agents is the potential for serious systemic adverse events without the possibility to curtail exposure to the agent. The LATTE-2 study implemented a period of cabotegravir and rilpivirine oral dosing, prior to long-acting cabotegravir or rilpivirine dosing, as a strategy to identify any early-onset acute safety issues before administering the long-acting injectable formulations. No drug hypersensitivity reactions were observed in the LATTE-2 study. An oral lead-in strategy has been implemented in phase III HIV treatment studies, to determine if there is a need for continued use of the oral lead-in. Injection-site reactions were common with intramuscular treatment, but most were short in duration and mild in severity, and rarely led to treatment discontinuation, consistent with previously reported studies with healthy adults. (Spreen W, Williams P, Margolis D, et al. Pharmacokinetics, safety, and tolerability with repeat doses of GSK1265744 and rilpivirine (TMC278) long-acting nano-suspensions in healthy adults. *J Acquir Immune Defic Syndr* 2014; 67 (5): 487-92).

The high satisfaction reported by subjects in the LATTE-2 study suggests that long-acting regimens may provide a preferential alternative to oral daily therapy for HIV-infected patients.[23] The acceptability and tolerability of injectable dosing options will be an important component of long-term treatment success, and a high degree of treatment satisfaction will avail this option for patients burdened by life-long daily oral medication compliance.

Results from the LATTE-2 study demonstrate high rates of efficacy and an acceptable safety profile for long-acting cabotegravir+rilpivirine as injectable two-drug maintenance therapy in virologically suppressed subjects with HIV. These results support the further evaluation of monthly long-acting cabotegravir+rilpivirine as the first ever injectable ART regimen.

What is claimed:

1. A method of treating HIV-1 infection in a subject in need thereof, comprising intramuscularly administering into a gluteus medius muscle of the subject effective amounts of cabotegravir and rilpivirine resulting in the subject having a viral load of less than or equal to 50 copies of HIV-1 virus particles per mL of blood plasma (≤50 c/mL) in the subject after at least 96 weeks of administration,
  wherein the effective amounts of cabotegravir and rilpivirine result in the subject having the viral load of ≤50 c/mL and comprise 400 mg of cabotegravir in a 2-mL injectable formulation and 600 mg of rilpivirine in a separate 2-mL injectable formulation administered once every four weeks or once a month.

2. The method of claim 1, wherein the effective amounts of cabotegravir and rilpivirine which result in the subject having the viral load of ≤50 c/mL are administered once every four weeks.

3. The method of claim 1, wherein the effective amounts of cabotegravir and rilpivirine which result in the subject having the viral load of ≤50 c/mL are administered once every month.

4. The method of claim 1, wherein the effective amounts of cabotegravir and rilpivirine which result in the subject having the viral load of ≤50 c/mL are administered once every four weeks or once a month, with a 14-day dosing window.

5. The method of claim 1, wherein the subject received oral anti-HIV therapy which was discontinued prior to the intramuscular administration.

6. The method of claim 5, wherein the oral anti-HIV therapy comprised once daily administration of cabotegravir or a pharmaceutically acceptable salt thereof and/or once daily administration of rilpivirine or a pharmaceutically acceptable salt thereof.

7. The method of claim 6, wherein the oral anti-HIV therapy comprised once daily administration of an amount by weight of the pharmaceutically acceptable salt of cabotegravir equivalent to 30 mg of cabotegravir and/or once daily administration of an amount by weight of the pharmaceutically acceptable salt of rilpivirine equivalent to 25 mg of rilpivirine.

8. The method of claim 1, wherein the method comprises intramuscularly administering into a gluteus medius muscle of the subject effective amounts of cabotegravir and rilpivirine resulting in the subject having a viral load of less than 50 copies of HIV-1 virus particles per mL of blood plasma (<50 c/mL) in the subject after at least 96 weeks of administration,
wherein the effective amounts of cabotegravir and rilpivirine result in the subject having the viral load of <50 c/mL and comprise 400 mg of cabotegravir in a 2-mL injectable formulation and 600 mg of rilpivirine in a separate 2-mL injectable formulation administered once every four weeks or once a month.

9. A method of treating HIV-1 infection in a subject in need thereof, comprising intramuscularly administering into a gluteus medius muscle of the subject effective amounts of cabotegravir and rilpivirine resulting in the subject having a viral load of less than or equal to 50 copies of HIV-1 virus particles per mL of blood plasma (≤50 c/mL) in the subject after at least 96 weeks of administration,
wherein the effective amounts of cabotegravir and rilpivirine result in the subject having the viral load of ≤50 c/mL and comprise 600 mg of cabotegravir in a 3-mL injectable formulation and 900 mg of rilpivirine in a separate 3-mL injectable formulation administered every once eight weeks or once every two months.

10. The method of claim 9, wherein the effective amounts of cabotegravir and rilpivirine which result in the subject having the viral load of ≤50 c/mL are administered once every eight weeks.

11. The method of claim 9, wherein the effective amounts of cabotegravir and rilpivirine which result in the subject having the viral load of ≤50 c/mL are administered once every two months.

12. The method of claim 9, wherein the effective amounts of cabotegravir and rilpivirine which result in the subject having the viral load of ≤50 c/mL are administered once every eight weeks or once every 2 months, with a 14-day dosing window.

13. The method of claim 9, wherein the subject received oral anti-HIV therapy which was discontinued prior to the intramuscular administration.

14. The method of claim 13, wherein the oral anti-HIV therapy comprised once daily administration of cabotegravir or a pharmaceutically acceptable salt thereof and/or once daily administration of rilpivirine or a pharmaceutically acceptable salt thereof.

15. The method of claim 14, wherein the oral anti-HIV therapy comprised once daily administration of an amount by weight of the pharmaceutically acceptable salt of cabotegravir equivalent to 30 mg of cabotegravir and/or once daily administration of an amount by weight of the pharmaceutically acceptable salt of rilpivirine equivalent to 25 mg of rilpivirine.

16. The method of claim 9, wherein the method comprises intramuscularly administering into a gluteus medius muscle of the subject effective amounts of cabotegravir and rilpivirine resulting in the subject having a viral load of less than 50 copies of HIV-1 virus particles per mL of blood plasma (<50 c/mL) in the subject after at least 96 weeks of administration,
wherein the effective amounts of cabotegravir and rilpivirine result in the subject having the viral load of <50 c/mL and comprise 600 mg of cabotegravir in a 3-mL injectable formulation and 900 mg of rilpivirine in a separate 3-mL injectable formulation administered once every eight weeks or once every two months.

17. A method of treating HIV-1 infection in a subject in need thereof, comprising intramuscularly administering into a gluteus medius muscle of the subject effective amounts of cabotegravir and rilpivirine which do not result in an emergent resistance-associated mutation in an HIV virus in the subject after at least 96 weeks of administration,
wherein the effective amounts of cabotegravir and rilpivirine comprise 400 mg of cabotegravir in a 2-mL injectable formulation and 600 mg of rilpivirine in a separate 2-mL injectable formulation administered every four weeks or once a month.

18. The method of claim 17, wherein the effective amounts of cabotegravir and rilpivirine are administered once every four weeks.

19. The method of claim 17, wherein the effective amounts of cabotegravir and rilpivirine are administered once every month.

20. The method of claim 17, wherein the effective amounts of cabotegravir and rilpivirine are administered once every four weeks or once a month, with a 14-day dosing window.

21. The method of claim 17, wherein the subject received oral anti-HIV therapy which was discontinued prior to the intramuscular administration.

22. The method of claim 21, wherein the oral anti-HIV therapy comprised once daily administration of cabotegravir or a pharmaceutically acceptable salt thereof and/or once daily administration of rilpivirine or a pharmaceutically acceptable salt thereof.

23. The method of claim 22, wherein the oral anti-HIV therapy comprised once daily administration of an amount by weight of the pharmaceutically acceptable salt of cabotegravir equivalent to 30 mg of cabotegravir and/or once daily administration of an amount by weight of the pharmaceutically acceptable salt of rilpivirine equivalent to 25 mg of rilpivirine.

24. A method of treating HIV-1 infection in a subject in need thereof, comprising intramuscularly administering into a gluteus medius muscle of the subject effective amounts of cabotegravir and rilpivirine which do not result in an emergent resistance-associated mutation in an HIV virus in the subject after at least 96 weeks of administration,
   wherein the effective amounts of cabotegravir and rilpivirine comprise 600 mg of cabotegravir in a 3-mL injectable formulation and 900 mg of rilpivirine in a separate 3-mL injectable formulation administered once every eight weeks or once every two months.

25. The method of claim 24, wherein the effective amounts of cabotegravir and rilpivirine are administered once every eight weeks.

26. The method of claim 24, wherein the effective amounts of cabotegravir and rilpivirine are administered once every two months.

27. The method of claim 24, wherein the effective amounts of cabotegravir and rilpivirine are administered once every eight weeks or once every 2 months, with a 14-day dosing window.

28. The method of claim 24, wherein the subject received oral anti-HIV therapy which was discontinued prior to the intramuscular administration.

29. The method of claim 28, wherein the oral anti-HIV therapy comprised once daily administration of cabotegravir or a pharmaceutically acceptable salt thereof and/or once daily administration of rilpivirine or a pharmaceutically acceptable salt thereof.

30. The method of claim 29, wherein the oral anti-HIV therapy comprised once daily administration of an amount by weight of the pharmaceutically acceptable salt of cabotegravir equivalent to 30 mg of cabotegravir and/or once daily administration of an amount by weight of the pharmaceutically acceptable salt of rilpivirine equivalent to 25 mg of rilpivirine.

* * * * *

UNITED STATES PATENT AND TRADEMARK OFFICE
CERTIFICATE OF CORRECTION

Page 1 of 1

PATENT NO. : 12,178,815 B2
APPLICATION NO. : 18/762939
DATED : December 31, 2024
INVENTOR(S) : Herta Crauwels et al.

It is certified that error appears in the above-identified patent and that said Letters Patent is hereby corrected as shown below:

In the Claims

In Claim 9, at Column 23, Line 54, delete "every once eight weeks" and insert --once every eight weeks-- therefor.

In Claim 17, at Column 24, Lines 38-39, delete "administered every four weeks" and insert --administered once every four weeks-- therefor.

Signed and Sealed this
Thirtieth Day of September, 2025

John A. Squires
*Director of the United States Patent and Trademark Office*